United States Patent [19]
Nemirovski et al.

[11] Patent Number: 6,024,700
[45] Date of Patent: Feb. 15, 2000

[54] SYSTEM AND METHOD FOR DETECTING A THOUGHT AND GENERATING A CONTROL INSTRUCTION IN RESPONSE THERETO

[76] Inventors: Guerman G. Nemirovski, 120-28 Ave. NE.; Gregory L. Troussov, 3391 Walnut St. NE., both of St. Petersburg, Fla. 33704

[21] Appl. No.: 09/116,720
[22] Filed: Jul. 16, 1998
[51] Int. Cl.$^7$ ..................................................... A61N 5/00
[52] U.S. Cl. ........................... 600/300; 600/544; 128/905
[58] Field of Search ..................................... 600/300, 544, 600/545, 378, 379; 607/136; 128/898, 899, 897, 905

[56] References Cited

U.S. PATENT DOCUMENTS

| | | |
|---|---|---|
| 3,870,034 | 3/1975 | James . |
| 4,064,870 | 12/1977 | Dumitrescu et al. . |
| 5,638,826 | 6/1997 | Wolpaw et al. . |
| 5,676,138 | 10/1997 | Zawilinski . |

OTHER PUBLICATIONS

*Archives of Physical Medicine and Rehabilitation,* "Answering Questions With an Electroencephalogram–Based Brain–Computer Interface", by Laurie A. Miner, MS, PT; Dennis J. McFrland, PhD.; and Jonathan R. Wolpaw, MD, taken from the Internet at http://www.archives–pmr.prg/abs79_9/v9n9p1029.html and http://silk,nig.gov/silk/ncmrr/abstract/absJRW1.htm, 3 pages.
*Devices read brain waves,* "They help paralyzed communicate", by Robert S. Boyd, taken from the Internet at http://www.freep.com/tech/qthink25.htm, 4 pages.
"Discover the Cyberlink™ Mind Mouse!", Reprinted from the Internet at http://www.mindmouse.com, Dec. 4, 1998, 1 page.
"The Cyberlink™ Mind Mouse", Reprinted from the Internet at http://www.mindmouse.com/Business/Productinfo.htm, Dec. 4, 1998, 2 pp.
"Brain Actuated Technologies", Reprinted from the Internet at http://www.mindmouse.com/Business/bat.htm, Dec. 4, 1998, 2 pp.
"The MindDrive Thought Response Technology", *The Other 90%,* Reprinted from the Internet at http://www.other90.come/new/htm/whitepage.htm, Jul. 9, 1998, 2 pp.

*Primary Examiner*—Cary O'Connor
*Assistant Examiner*—Michael Astorino
*Attorney, Agent, or Firm*—Renner, Otto, Boisselle & Sklar, P.L.L.

[57] ABSTRACT

A method of detecting a thought and generating a control instruction corresponding to the thought includes detecting the thought by monitoring air pressure near a human ear when a user is thinking. In addition, the method includes providing a control instruction corresponding to the detected thought. A system for detecting a thought and generating a control instruction corresponding to the thought is also disclosed and includes a pressure sensor for sensing a pressure near a human ear when a user is thinking, wherein the sensor produces an electrical signal corresponding to the pressure. A processor processes the electrical signal to detect the thought, generates the control instruction in response to the detection, and sends a control instruction to an output peripheral which provides an output control function corresponding to the control instruction.

20 Claims, 12 Drawing Sheets

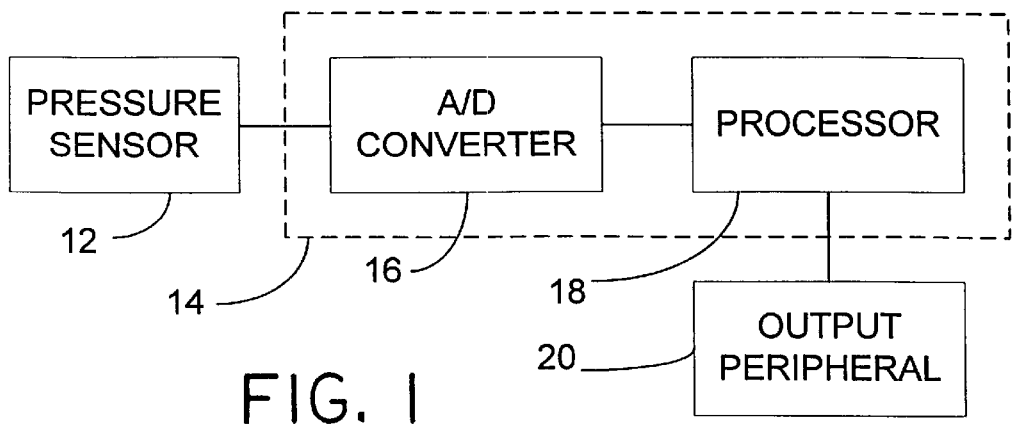
FIG. 1
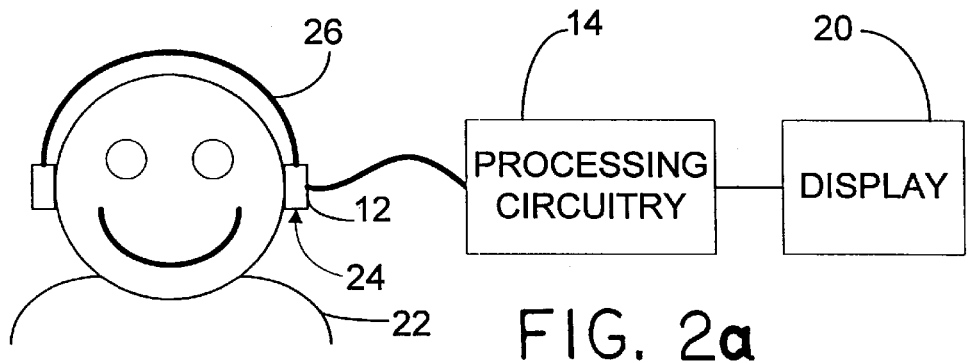
FIG. 2a
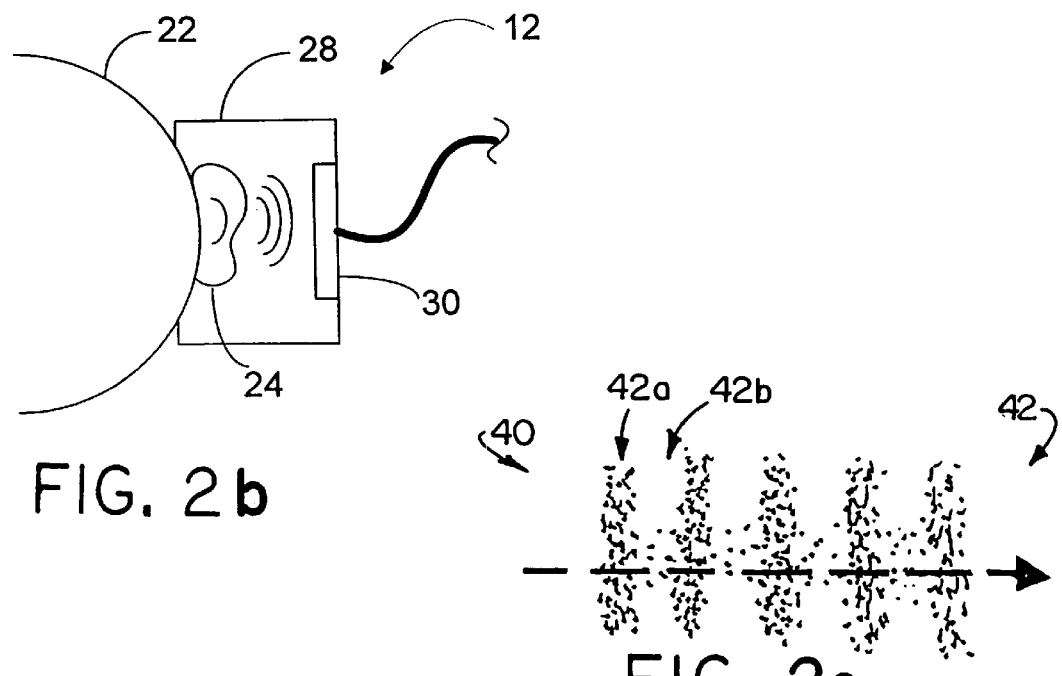
FIG. 2b
FIG. 2c

SYSTEM AND METHOD FOR DETECTING A THOUGHT AND GENERATING A CONTROL INSTRUCTION IN RESPONSE THERETO

FIELD OF THE INVENTION

The present invention generally relates to detecting mental activities such as thoughts using a sensor and providing system control functions in response to the detected mental activities. More particularly, the present invention detects thoughts by analyzing changes in air pressure near the human ear and processing the collected data to determine a proper control functionality corresponding to the thought.

BACKGROUND OF THE INVENTION

For many years attempts have been made to decipher one's thoughts using the bio-electric signals that are produced by the body involuntarily in response to the thoughts or emotions. Traditional biofeedback techniques have focused on measuring the conductivity and electrical sensitivity of the skin using, for example, galvanic skin response (GSR) and electrodermal reflex (EDR). The prior art techniques, however, are slow since the body chemistry which impacts the above physical characteristics does not change quickly. The slow electro-chemical response results in a delay of several seconds in detecting the thought or emotion. Such limitations have therefore suffered from lacking a real-time response functionality required or desired in many control function environments.

One exemplary solution to the above problems in the prior art uses a sensor sleeve that fits over the human finger. The sensor appears to utilize a pair of electrodes for generating a current through the finger and also irradiates the skin with ultraviolet (UV) light to detect heart beat activity (e.g., the pulse), temperature (e.g., changes in resistivity), blood pulse volume and composite neural activity. The prior art sensor system processes the plurality of detected parameters as a series of electrical signals produced by the thoughts. The sensor technology, however, suffers from a variety of performance and other limitations. For example, the technology still is slow since the detected body parameters such as blood pulse volume and body temperature still are rather slow, thereby prohibiting a real-time type control functionality. In addition, the sensor is only capable of binary type control functionality such as ON/OFF, STOP/GO or UP/DOWN. Since many types of control systems require more than two control states, the above prior art solution is ineffective. Lastly, the sensor is not passive, but rather actively invades the human body with current and other electrical stimulus and irradiates the body with radiation such as ultraviolet light which have uncertain health and environmental impacts. Due to such uncertainty, many individuals are reticent to utilize the technology.

Therefore there is a need in the art for a system and a method for detecting thoughts and providing a control function in response to the detection in real-time. In addition, there is a need in the art for a system and method in which the detection of thoughts is accomplished with a passive sensor which does not output a voltage or radiation to detect a parameter, and lastly a system and method which provides a variety of control functions.

SUMMARY OF THE INVENTION

The present invention relates to a system and a method of detecting thoughts and providing one or more control instructions in response to the detection which corresponds to the thought. The invention includes a passive monitoring of air pressure near the human ear. The air pressure information is collected and processed to detect the presence of a thought and determine the type of thought conveyed. Once determined, a control instruction is provided which corresponds to the thought to effectuate a system control functionality.

According to one aspect of the present invention, the air pressure is monitored and collected by a pressure transducer such as a microphone which is located near the human ear. The microphone produces an analog electrical signal which corresponds to the sensed changes in air pressure with respect to time. According to the present invention, a person's thoughts provide changes in air pressure near the ear which are substantially unique for each of a plurality of thoughts. Thus, the detected changes in air pressure are used to detect the presence and the type of thought.

According to another aspect of the present invention, analog electrical signals, which are produced by the pressure sensor in response to the monitored air pressure, are converted into digital signal data, processed and analyzed to detect the presence and type of thought. According to one exemplary embodiment of the invention, the digital signal data is converted from the time domain to the frequency domain to separate data relating to a thought from noise. The data corresponding to a detected thought is then further processed and correlated with a plurality of data sets corresponding to particular thoughts to determine the type of thought. Subsequently, a control instruction is provided for effectuating a control function which corresponds to the detected thought.

According to yet another aspect of the present invention, a plurality of data sets corresponding to particular thoughts are constructed in conjunction with a calibration or practice mode. In such a mode, a person places the pressure sensor near their ear and thinks a particular thought while substantially concurrently indicating the type of thought manually (e.g., pushing a button or manipulating a joystick to indicate a particular function such as a jump or kick) one or more times to provide an exemplary thought signature for subsequent correlation. Preferably, the practice mode continues a plurality of times for each type of thought required for the control application. For each set of collected data for a given thought, statistical models may be used to characterize a typical thought signature in terms of its average and its standard deviation at various points in the data set which may then be subsequently used in the correlation analysis.

According to still another aspect of the present invention, a system for detecting thoughts and providing one or more control instructions in response thereto includes a pressure sensor which detects changes in air pressure near the ear. The pressure sensor may include a transducer such as a microphone which translates the changes in air pressure to an electrical signal which is processed using a system processor. The processor performs various forms of signal processing to detect a thought, determine the type of thought, and provide one or more control instructions to an output peripheral for effectuating the desired control function. Thus the output peripheral may include one or more of a vast array of peripherals such as a display, a medical device, industrial equipment, etc. The system of the present invention is unique since the human ear, traditionally viewed as an input device for processing sound waves or air pressure changes for conversion into sound by the human brain, is utilized and monitored as an output device to generate air pressure changes due to thoughts produced in the brain. The air pressure changes caused in the ear are therefore used as bio-signals and are processed to detect the occurrence and the type of thoughts for use in control functions.

In accordance with the present invention, the changes in air pressure near the ear occur and are detected quickly to thereby provide a substantially real-time control system. In addition, since the changes in air pressure are substantially unique for various thoughts, multiple control functions are available as opposed to the binary control capability of the prior art. Lastly, the pressure sensor is passive and therefore does not raise any potential health and/or environmental concerns.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

Although the invention is shown and described with respect to the embodiments below, it is obvious that equivalents and modifications will occur to others skilled in the art upon the reading and understanding of the specification. The present invention includes all such equivalents and modifications, and is limited only by the scope of the claims.

BRIEF DESCRIPTION OF THE DRAWINGS

FIG. 1 is a block level diagram illustrating a system by which a thought is detected and used to provide a control function which corresponds to the detected thought according to the present invention;

FIG. 2a is an environmental view of a user having a pressure sensor located near their ear which is in electrical communication with a processor coupled to a display according to the present invention;

FIG. 2b is an enlarged view of a portion of FIG. 2a illustrating in greater detail the pressure sensor monitoring air pressure near the ear according to one aspect of the present invention;

FIG. 2c is a pictorial representation of a wave in air, representing a plurality of longitudinal, molecular density changes according to the present invention;

DETAILED DESCRIPTION OF THE INVENTION

Figure 2D:
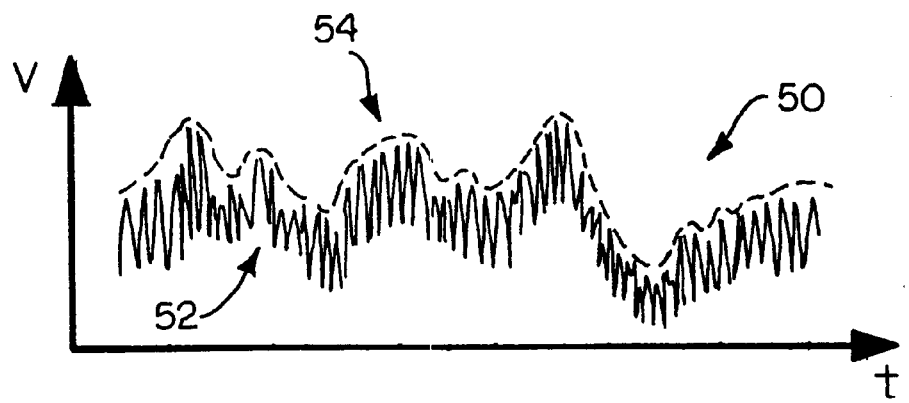
FIG. 2d is a graph illustrating an exemplary electrical signal produced by a transducer associated with the pressure sensor which indicates changes in air pressure at a location local to the pressure sensor according to the present invention.

The following is a detailed description of the present invention made in conjunction with the attached Figures, wherein like reference numerals will refer to like elements throughout. The present invention relates to a system and a method of detecting thoughts and providing one or more control instructions in response to the detection. Whereas prior art technologies relied upon the analysis of slow, electro-chemical reactions in the body to detect thoughts or emotions, the present invention monitors changes in air pressure near the human ear which occur nearly instantaneously in response to a thought to provide a substantially real-time detection and control system. In addition, the monitoring of the air pressure is passive and thus avoids potential health and/or environmental concerns related to subjecting the body to electrical signals and radiation. Furthermore, the changes in air pressure uniquely correspond to one of a variety of thoughts (e.g., have unique signal signatures) which allows a plurality of different thoughts to be detected and distinguished for a system requiring multiple control functions.

According to one aspect of the present invention, a system for detecting a thought and providing a corresponding control instruction in response to the detection includes a pressure sensor which is positioned near the ear of the user. The sensor is in electrical communication with processing circuitry and senses changes in air pressure near the ear due to the user's thoughts and converts the air pressure changes into an electrical signal. The electrical signal is then processed by the circuitry to detect the presence and the type of thought within the electrical signal and provide a control instruction which corresponds to the particular thought to an output peripheral for execution of the control instruction to effectuate a control function. Exemplary control functions may include, but are not limited to: controlling a video game display, controlling a piece of medical equipment such as a wheelchair, and controlling computer functions to effectuate a handless mouse.

According to another aspect of the present invention, a method of detecting a thought and providing a control instruction corresponding to the thought is provided. Thoughts are monitored by monitoring the air pressure wherein the air pressure changes near the ear correspond to thoughts and noise. The method includes converting the air pressure data to an analog electrical signal which is subsequently converted into digital signal data for further processing. Data signal processing is implemented to analyze the data and separate noise from thought data to thereby detect the presence of a thought. Further processing is then used to determine the type of thought detected and provide one or more control instructions to an output peripheral for execution of the appropriate control functions.

In a preferred embodiment of the present invention, the pressure sensor and transducer includes a microphone and the data signal processing includes conversion of data segments into the frequency domain to distinguish data relating to a thought from noise. Once a thought is detected, further data processing includes correlation between the signal data in the frequency domain to a plurality of frequency domain data sets. If a resulting correlation coefficient exceeds a predetermined threshold, the type of thought is determined and one or more control instructions which correspond to the thought are retrieved from a memory and sent to an output peripheral for execution of the instructions, thereby providing system control functionality.

Turning now to the Figures, a detailed description of the invention follows. FIG. 1 is a block level diagram which illustrates a system 10 for detecting a thought and providing one or more control instructions which correspond to the detected thought. The system 10 includes a pressure sensor 12 coupled to processing circuitry 14 including an analog-to-digital (A/D) converter 16, such as a PCI9118HG data acquisition card manufactured by Adlink Technology or a DAQi250 data acquisition card manufactured by Ines Company Gmbh in Germany, for converting an analog signal into digital signal data. The processing circuitry 14 also includes a processor 18 for receiving the digital signal data from the A/D converter 16 and performing various signal processing functions on the digital signal data to detect the presence of a thought and determine the type of thought. The system 10 also includes an output peripheral 20 coupled to the processor 18 for executing one or more control instructions provided by the processor 18 which correspond to the detected thought.

The system 10 is illustrated within an exemplary environmental context in FIG. 2a. In FIG. 2a, a user 22 has the pressure sensor 12 located near the ear 24 by locating the pressure sensor 12 within a pair of headphones 26. The headphones 26 preferably provide two functions: (1) they locate the pressure sensor 12 near the ear in a relatively fixed position, and (2) they provide a modest amount of external sound insulation, thereby lessening the amount of external noise detected by the pressure sensor 12. When the user 22 thinks a particular thought, a change in air pressure occurs in or near the ear 24, wherein the air pressure change uniquely identifies the thought. The change in air pressure is detected by the pressure sensor 12 and preferably converts the detected air pressure into an analog electrical signal for subsequent processing by the circuitry 14. In FIG. 2a, the exemplary output peripheral 20 is illustrated as a display which carries out the control instruction (e.g., executing a punch or a kick in a video game).

The positional relationship between the pressure sensor 12 and the ear 24 is illustrated in greater detail in FIG. 2b. The pressure sensor 12 includes a housing 28 such as a headphone housing which has a sensor, preferably a microphone 30, affixed thereon. The manner in which the microphone 30 is attached to the housing 28 may vary in order to adjust the distance at which the microphone 30 is from the ear 24. Preferably, the microphone 30 is near the ear 24, for example, within about 1 inch to 2 inches, depending upon the sensitivity of the microphone, however, other distances may also be used and are contemplated as falling within the scope of the present invention. More preferably, the microphone 30 is located comfortably within the ear 24 or as close as possible to the ear to receive the air pressure changes at an increased intensity level. In FIG. 2b neither the shape nor the position of the microphone 30 is drawn to scale, but rather is merely illustrated in this manner for the sake of clarity.

In a preferred embodiment of the present invention, the microphone 30 has a sensitivity of at least about 47 mV/Pa (millivolts per pascal) and even more preferably a sensitivity of about 100 mV/Pa or more with a frequency range of about 10 Hz to about 800 Hz. One exemplary microphone which may be used is the Model 4190 microphone manufactured by Bruel & Kjaer in Denmark. Alternatively, however, other types of microphone or other type pressure sensor may by used and each such alternative is contemplated as falling within the scope of the present invention. Using the Model 4190 microphone the analog output signal is about 400 mV peak-to-peak. The amplitude of the output signal, however, depends upon the amplitude coefficient of the electronics and the position of the microphone with respect to the ear and thus may vary substantially.

It is not certain what physical, chemical or neural mechanism causes or generates the changes in air pressure in or near the ear in response to various thoughts. It is hypothesized that various thoughts have varying intensities which cause involuntary muscle contractions or movements on a microscopic level in or near the ear, which generate pressure changes in or near the ear due to the compression of the air local to the ear. Nevertheless, regardless of the exact physical, chemical or neural mechanism, empirical testing has confirmed that thoughts generate small pressure changes in or near the ear of the person having the thoughts and that the air pressure changes have substantially their own signature and are thus substantially unique for each type of thought. Consequently, the air pressure changes can be monitored near the ear and used to detect the presence and type of thoughts of a user.

The present invention uses the term "changes in air pressure" near the ear in its most broad sense to characterize the parameter being measured. Changes in air pressure may alternatively be characterized as sound waves. As is well known by those skilled in the art, a sound wave is a longitudinal wave in which "pushes" are communicated from molecule to molecule within the medium (which in this preferred embodiment is air). The restoring force for such a wave is due to the pressure of the air; wherever the density of molecules is higher than normal, the pressure also is higher than normal and pushes the molecules apart. FIG. 2c illustrates an exemplary sound wave 40 in air, and consists of a plurality of alternating zones 42 of low and high molecular density 42a and 42b, respectively. The varying molecular density results in changes in air pressure having a particular frequency as the sound wave propagates. In addition, as is well known by those skilled in the art, as a sound wave spreads out from its source, its intensity falls off because as the area of the wave grows larger, the total energy is constant. Therefore the energy per unit area decreases with the inverse square of the distance. Consequently, it is desirable to have the microphone 30 sufficiently close to the ear 24 so that the intensity level of the air pressure changes will be larger and thus easier to detect over any noise.

The frequency range at which sound waves are audible is about 20 Hz to about 20 KHz, however, the present invention is not concerned with whether the air pressure changes are audible since the microphone 30 is sufficiently sensitive and has a frequency detection range which is sufficient to detect air pressure changes at high or low frequencies. In a preferred embodiment of the invention, a frequency range of about 10 Hz to about 800 Hz is focused upon since it has been determined via empirical testing that sufficient data is available within that frequency range to detect and identify a thought. Alternatively, however, any frequency range may be monitored and such variations are contemplated as falling within the scope of the present invention.

The pressure sensor 12 (preferably including the microphone 30) monitors the changes in air pressure and converts the pressure data to an analog electrical signal 50, as illustrated in FIG. 2d. Note that in the signal 50 there are at least two signal components, a high frequency component 52 and a low frequency component 54. In addition, other frequencies may also exist within the electrical signal 50 and the present invention preferably analyzes the various signal frequencies in the subsequent data processing performed by the processor 18, which will be described in greater detail below.

Figure 3:
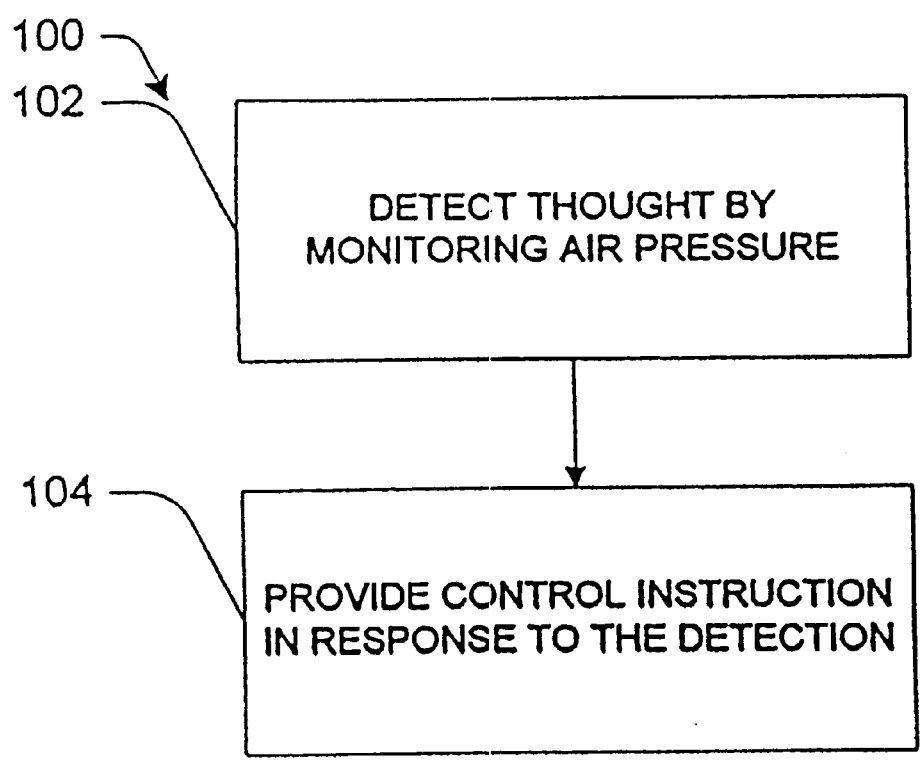
FIG. 3 is a flow chart diagram illustrating a method of detecting a thought and providing a control instruction in response to the detected thought according to the present invention.

A method 100 for carrying out the present invention is disclosed in FIG. 3. The method 100 includes detecting a thought by monitoring a change in air pressure caused by one's thoughts at step 102. Once the thought is detected at step 102, one or more control instructions which correspond to the detected thought is provided to an output peripheral at step 104 to effectuate the desired control function.

Figure 4:
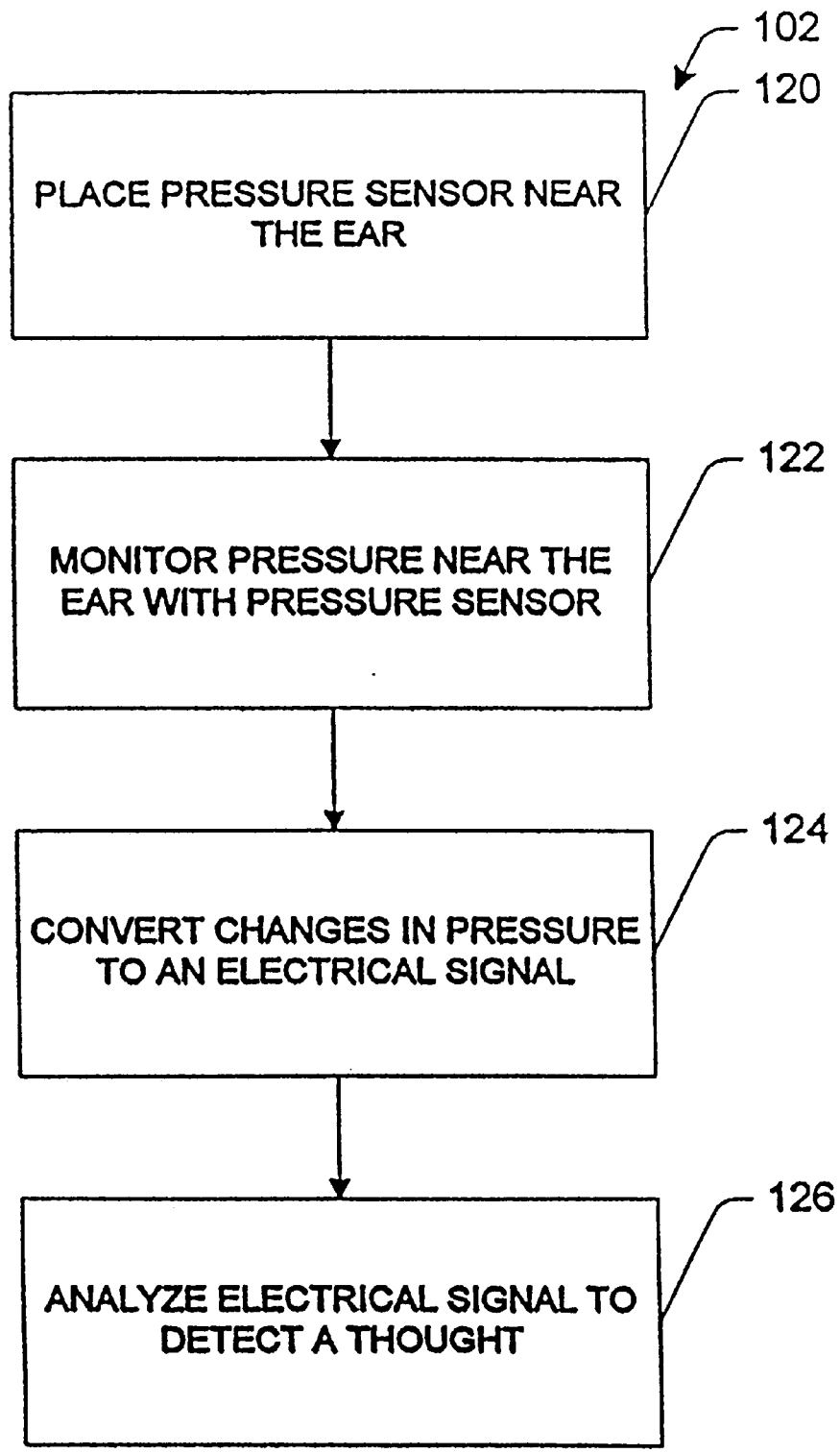
FIG. 4 is a flow chart diagram illustrating a method of monitoring the air pressure according to the present invention.

The preferred method of detecting a thought (step 102) is provided in FIG. 4. A pressure sensor such as the one disclosed in conjunction with FIGS. 1 and 2a–2d is placed near the ear of the user who's thoughts are to be detected at step 120. According to a preferred embodiment of the present invention, air pressure changes near the ear occur in response to thoughts and thus the pressure sensor is placed near the ear at step 120. Alternatively, however, since thoughts may result in pressure changes at or near other parts of the body, it is contemplated that in alternative embodiments of the present invention the pressure sensor may be located on or near other parts of the body and any detection of thoughts by analyzing changes in air pressure is contemplated as falling within the scope of the present invention.

The air pressure near the ear is monitored with the sensor at step 122 and is converted to an electrical signal at step 124 for subsequent analysis. After conversion into an electrical signal at step 124, the electrical signal is analyzed to detect a thought at step 126. Although it is conceivable that the thought may be detected at step 126 simply by analyzing the signal corresponding to changes in air pressure without additional data processing, it is preferable that the thought detection process of step 126 include data processing in conjunction with the signal analysis.

Figure 5:
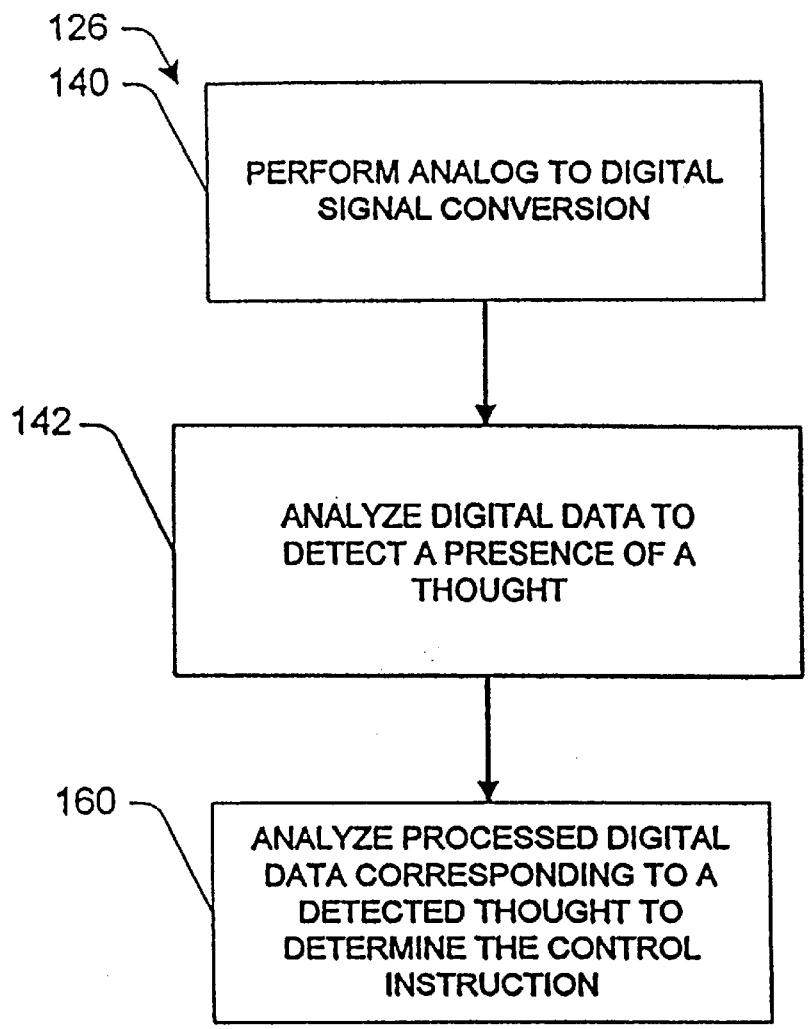
FIG. 5 is a flow chart diagram illustrating a method of processing an electrical signal corresponding to the air pressure for detecting a thought.
Figure 6:
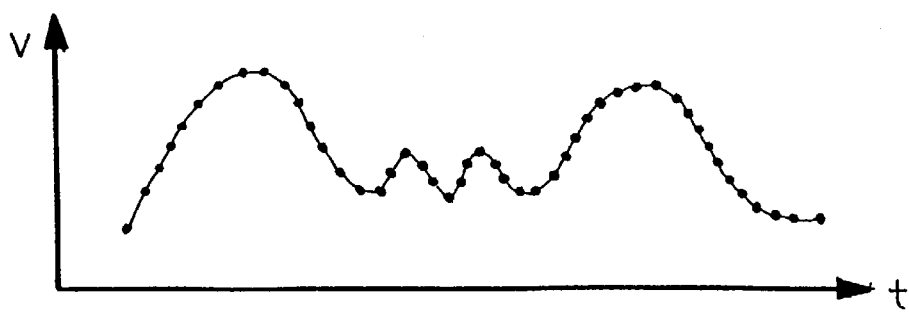
FIG. 6 is a graph illustrating the conversion of an analog electrical signal to digital signal data according to the present invention.

A method of analyzing and processing the electrical signal which corresponds to the monitored pressure is illustrated in FIG. 5. The electrical signal, which is an analog signal as illustrated in FIG. 2d, is converted into a digital signal at step 140, as illustrated in FIG. 6. As is well known by those skilled in the art, an analog signal may be converted into a digital signal by sampling the analog signal at a selected frequency and identifying the signal amplitude at each sampling point. Each sampled data point is then saved as a digital word in a memory and used for further analysis. In FIG. 6, a sampled analog signal is illustrated in which the dotted line illustrates the exemplary analog signal for a particular time period and the plurality of points on the dotted line represent sampled amplitude values which are saved in the memory. It is desirable that the sampling frequency be sufficient to capture enough data points to adequately represent the analog signal. Preferably, the sampling rate of the present invention is 32 KHz and the total signal time length to be analyzed is 2048 mSec. Alternatively, however, other sampling rates and data acquisition time frames may be utilized and such variations are contemplated as falling within the scope of the present invention.

Figure 7:
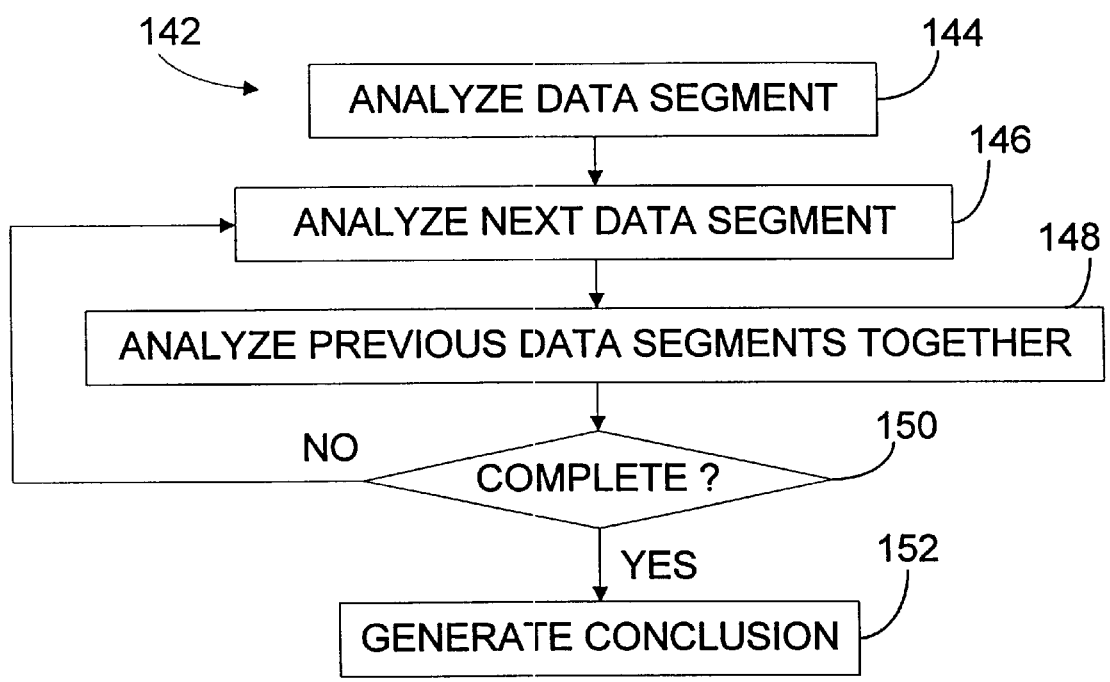
FIG. 7 is a flow chart diagram illustrating a method of analyzing the digital signal data according to the present invention.
Figure 8:
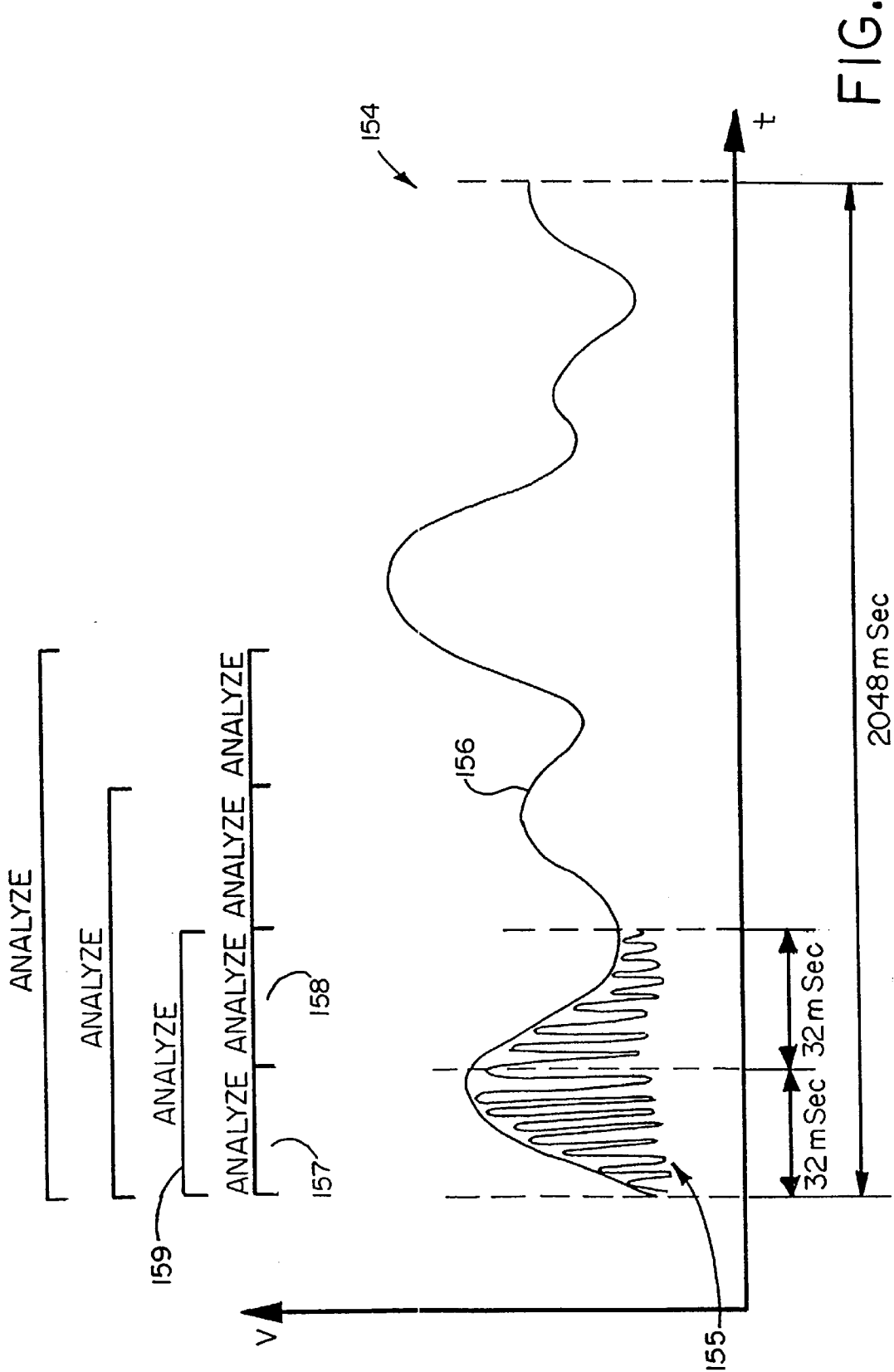
FIG. 8 is a graph illustrating a method of analyzing the digital signal data with the flow chart of FIG. 7 according to the present invention.

Once the analog signal has been converted into digital signal data at step 140, the digital data is analyzed and processed by, for example, a signal processor to detect the presence of a thought at step 142. Preferably, the analysis and processing of the data is performed in a plurality of segments, as illustrated in FIGS. 7 and 8. As illustrated in FIG. 7, a first data segment is analyzed at step 144, followed by the analysis of a second data segment at step 146. Once various data segments have been analyzed separately, the data segments are analyzed together at step 148. If all the data segments have not yet been analyzed at step 150, the method 142 returns to step 146 and the next data segment is analyzed, after which all previous segments are then analyzed together at step 148. The process continues until all the data segments have been analyzed at step 150, thus allowing a conclusion to be generated using the analyzed data segments at step 152.

The data segment analysis may be seen graphically in FIG. 8, wherein digital signal data 154 is illustrated as being continuous for the sake of simplicity. The total length of data for analysis is preferably separated into 64 segments that are each 32 mSec in length. Note that the signal 154 contains both a high frequency component 155 and a low frequency component 156. Since data relating to a thought potentially may be found in either component or the thought data may span multiple data segments, it is preferred that the data segments be analyzed separately as well as together. Thus, at step 144 of FIG. 7, the first data segment is analyzed (region 157), at step 146 the second data segment is then analyzed (region 158) and at step 148 both data segments are analyzed together (region 159). The process then continues for all the data segments; consequently, the data analysis of the present invention preferably analyzes both the high frequency and low frequency signals to detect the thought since empirical testing has shown that signals of interest typically fall in the range of about 10 Hz to about 800 Hz.

Returning back to FIG. 5, once the data considered to be thought data has been found in the pressure data at step 142, subsequent analysis is performed to determine the type of the detected thought at step 160. Preferably, such analysis includes correlation between the detected signal and a plurality of stored data sets which correspond to pre-identified thoughts. If the detected signal data correlates within a predetermined amount (typically identified by a correlation coefficient) with one of the stored data sets, the type of thought has been determined and one or more control instructions which correspond to that particular thought may then be retrieved and sent to the output peripheral to provide the desired control function. Alternatively, however, other techniques may be utilized to identify the thought type once the thought is detected and any such technique is contemplated as falling within the scope of the present invention.

Figure 9:
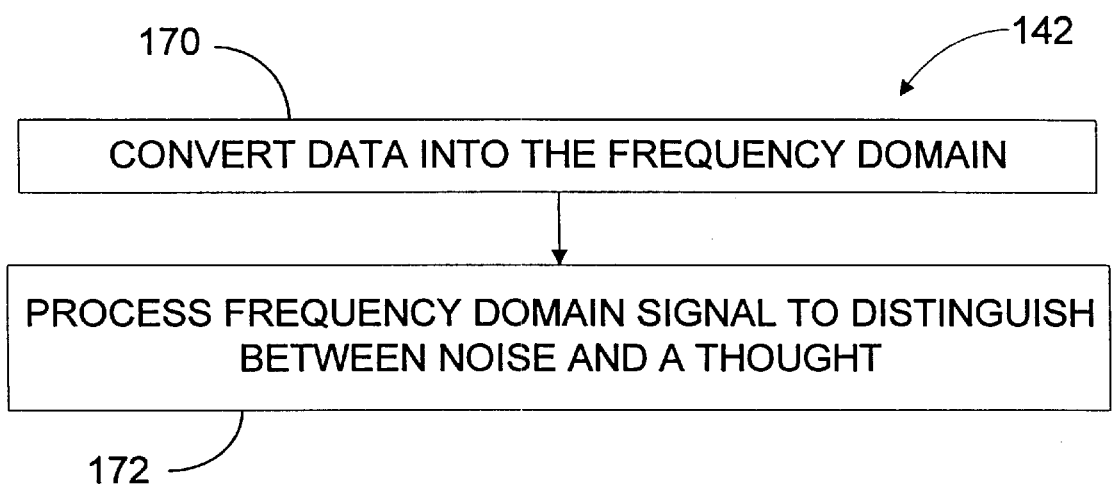
FIG. 9 is a flow chart diagram illustrating a method of processing the digital signal data according to the present invention.

One exemplary method of analyzing the digital signal in data segments is illustrated in FIG. 9. For each data segment of 32 mSec, the data is converted from the time domain to the frequency domain at step 170 using, for example, a Fast Fourier Transform (FFT) as is well known by those skilled in the art. As is well known, a time domain signal f(t) is linked with the frequency domain f($\omega$) according to the following equation:

$$F(f(t)) = \int f(t) e^{-j\omega t} dt = f(j\omega),$$

wherein F(f(t)) is a traditional Fourier transform. As is well known by those skilled in the art, a Fast Fourier Transform is related to the traditional Fourier transform since the Fast Fourier Transform is an efficient algorithm for computing discrete Fourier transforms. After the digital signal data is converted into the frequency domain via the Fast Fourier Transform, the frequency domain data is processed to distinguish data relating to thoughts from noise data at step 172. As is well known by those skilled in the art, the separation of data from noise is often simplified in the frequency domain because unlike noise, the data signal has some physical characteristics. Though the data signal in the time domain has an amplitude which is less than the noise, the data signal has a greater amplitude than the noise in the frequency domain. Therefore the Fast Fourier Transform is a typical method for noise separation.

The details surrounding the data processing of the digital signal data may be accomplished through a variety of data processing techniques as is well known by those skilled in the art and any data processing methodology is contemplated as falling within the scope of the present invention. Although many different data processing methodologies may be employed, the preferred methodology is disclosed below in conjunction with the following method.

Figure 10:
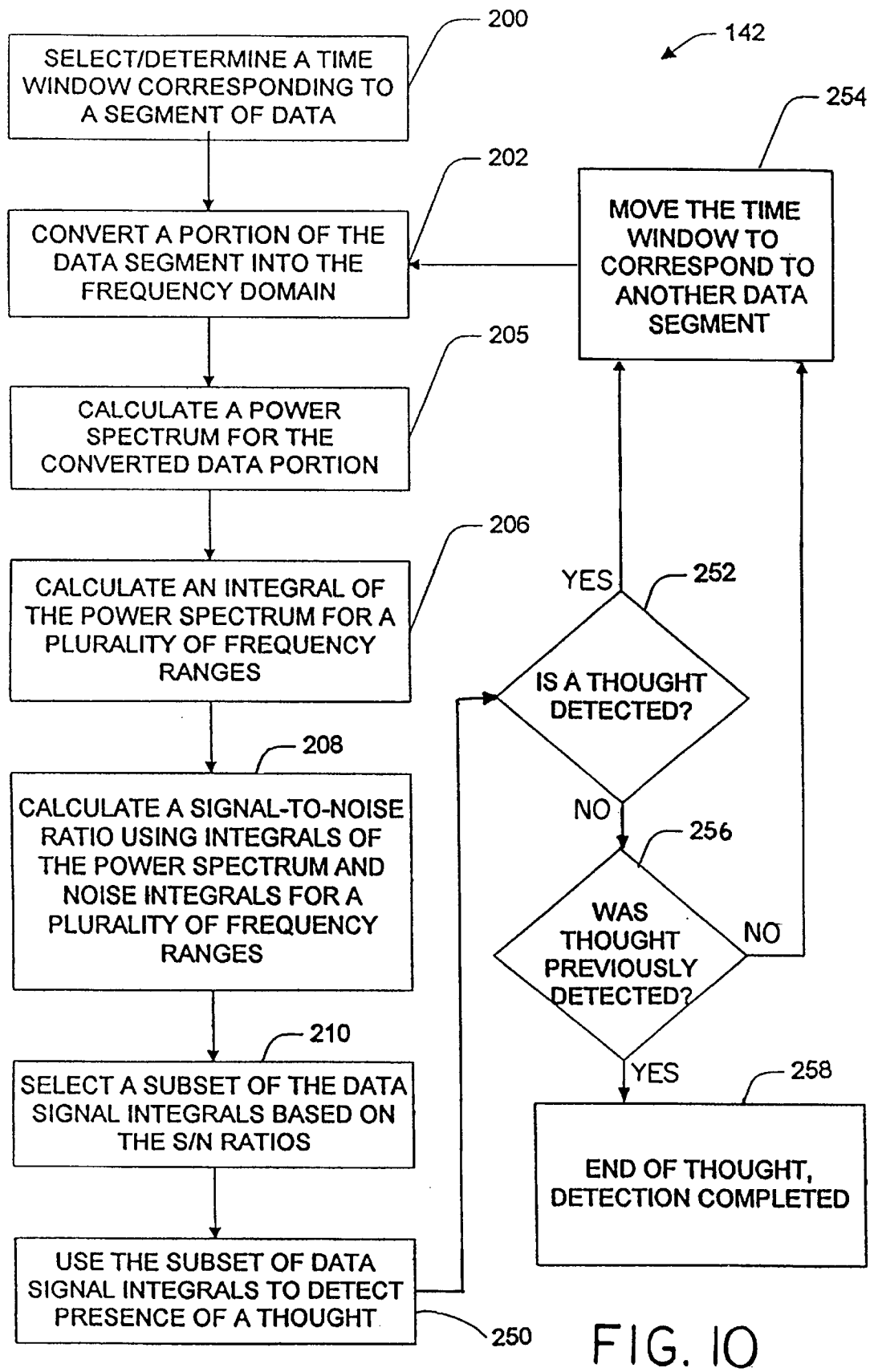
FIG. 10 is a flow chart diagram illustrating a method of processing the digital signal data according to the present invention.
Figure 11:
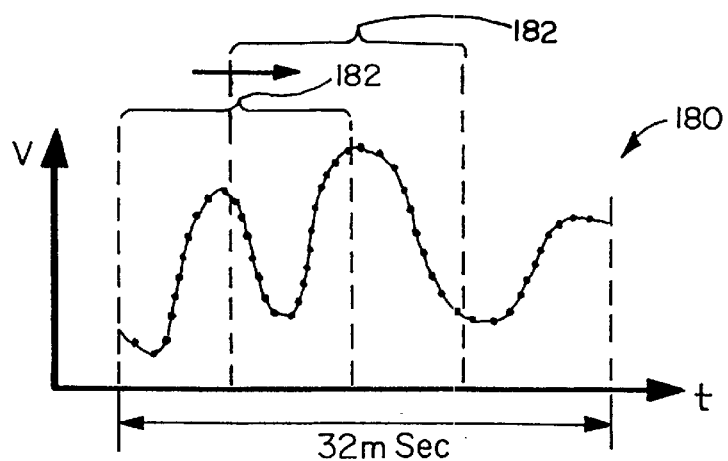
FIG. 11 is a graph illustrating the selection of a time window corresponding to a digital signal data segment according to the present invention.
Figure 12:
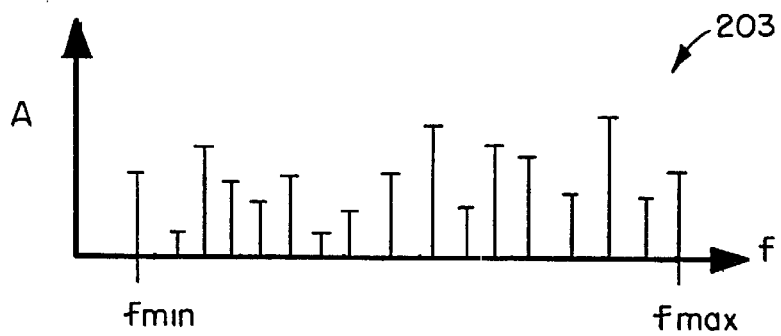
FIG. 12 is a graph illustrating an exemplary frequency domain representation of the digital signal data segment of FIG. 11 according to the present invention.

According to a preferred embodiment of the present invention, the data processing of step 142 of FIG. 5 is illustrated in detail in FIG. 10. As discussed in conjunction with FIGS. 7 and 8, the digital signal data having a total acquisition time length of 2048 mSec is separated into a plurality of data segments. For each data segment 180 being 32 mSec long, as illustrated in FIG. 11, a time window 182 corresponding to a portion of the data segment 180 is selected at step 200. According to a preferred embodiment of the present invention, the time window 182 is 16 mSec long and therefore constitutes one-half of the data segment. The data of the data segment portion within the time window 182 is then converted from the time domain into the frequency domain at step 202 using, for example, FFT techniques, thus resulting in a frequency spectrum 203 as illustrated in FIG. 12. Note that the details of FIG. 12 do not necessarily coincide with the digital signal of FIG. 11, but rather is provided simply for the sake of clarity. As illustrated in FIG. 12, $f_{MIN}$ is related to the total time of signal acquisition (in this particular embodiment is 2048 mSec and thus $f_{MIN}$ is equal to 0.5 Hz) and $f_{MAX}$ is equal to the Nyquist frequency which may vary, but in this particular example is equal to 16 KHz.

Figure 13:
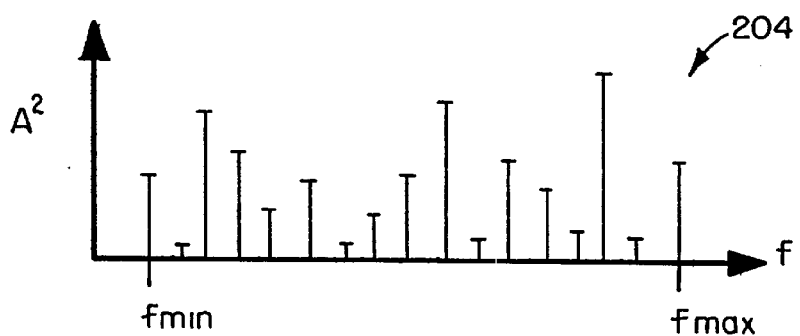
FIG. 13 is a graph illustrating a power spectrum of the frequency domain representation of FIG. 12 according to the present invention.

The frequency domain data of FIG. 12 is then further processed by calculating the power spectrum 204 for the converted data portion at step 20, which is illustrated graphically in FIG. 13. As is well known by those skilled in the art, the power spectrum may be determined by calculating the square of the frequency spectrum data.

The power spectrum 204 of FIG. 13 is then further processed by summing the power amplitudes within a plurality of frequency ranges which are preferably defined during a calibration process for each thought, wherein calibration is a process of applying the method in the situation when a user is tuning the system for each thought. Experimentally, it has been found that the number of ranges may vary between 20 to 50 and the frequency ranges need not be of equal length. For example, for the thought "kick", twenty-six (26) frequency ranges were used as follows:

| | | |
|---|---|---|
| Range 1: 41.7–44.2 Hz | Range 10: 174.9–176.3 Hz | Range 19: 464.9–469.7 Hz |
| Range 2: 58.5–60.1 Hz | Range 11: 208.7–211.7 Hz | Range 20: 481.5–483.2 Hz |
| Range 3: 72.5–76.8 Hz | Range 12: 216.4–219.8 Hz | Range 21: 601.3–604.9 Hz |
| Range 4: 96.2–98.9 Hz | Range 13: 271.6–274.1 Hz | Range 22: 621.7–625.6 Hz |
| Range 5: 99.8–104.4 Hz | Range 14: 292.2–296.0 Hz | Range 23: 638.5–640.0 Hz |
| Range 6: 115.5–118.6 Hz | Range 15: 305.3–310.6 Hz | Range 24: 672.8–673.9 Hz |
| Range 7: 125.3–126.1 Hz | Range 16: 374.2–374.9 Hz | Range 25: 712.0–717.3 Hz |
| Range 8: 128.5–132.9 Hz | Range 17: 392.7–395.0 Hz | Range 26: 762.2–765.5 Hz |
| Range 9: 151.1–153.5 Hz | Range 18: 450.1–452.5 Hz | |

Figure 14:
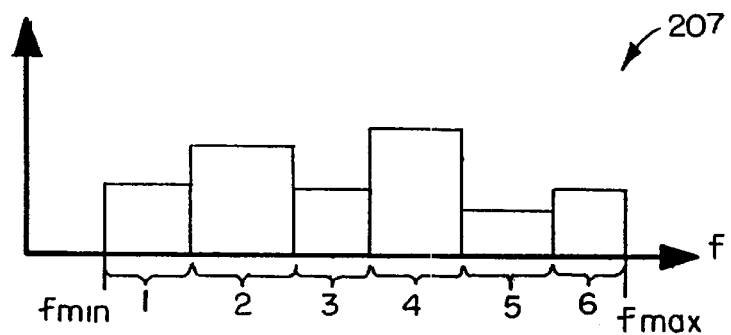
FIG. 14 is a graph illustrating integrals of the power spectrum of FIG. 13 for a plurality of frequency ranges according to the present invention.

For each separate range the power spectrum data within the range is utilized to calculate an integral 207 of the power spectrum at step 206 which effectively comprises a sum of the power amplitudes for each data point within each a particular frequency range. Exemplary integrals 207 for each range are illustrated graphically in FIG. 14. Note that in FIG. 14, only six frequency ranges are illustrated for purposes of clarity. Preferably, however, 20 to 50 such ranges will exist, although other numbers of frequency ranges are contemplated as falling within the scope of the present invention.

Once the integrals 207 for the signal data are calculated at step 206, noise data is used to calculate signal-to-noise ratios (S/N) for each of the frequency ranges at step 208 of FIG. 10. Noise data is preferably acquired by monitoring air pressure data using the pressure sensor before thoughts are detected. Then, the recorded noise data is converted into the frequency domain, a noise power spectrum is generated and noise integrals are calculated for the plurality of frequency ranges in a manner similar to the signal data as discussed above. The integrals 207 of the signal data (S) and the noise data integrals (N) (not shown) are used to calculate the signal-to-noise ratio (S/N) for each frequency range using the formula:

$$S/N = (S-N)/N \times 100\%.$$

Once the signal-to-noise ratio (S/N) for each frequency range is calculated, the ratio is compared to a predetermined threshold (preferably the threshold is equal to 20% which was determined empirically) and the comparison is used to select a subset of the data signal integrals 207 at step 210 for further analysis.

Figure 15:
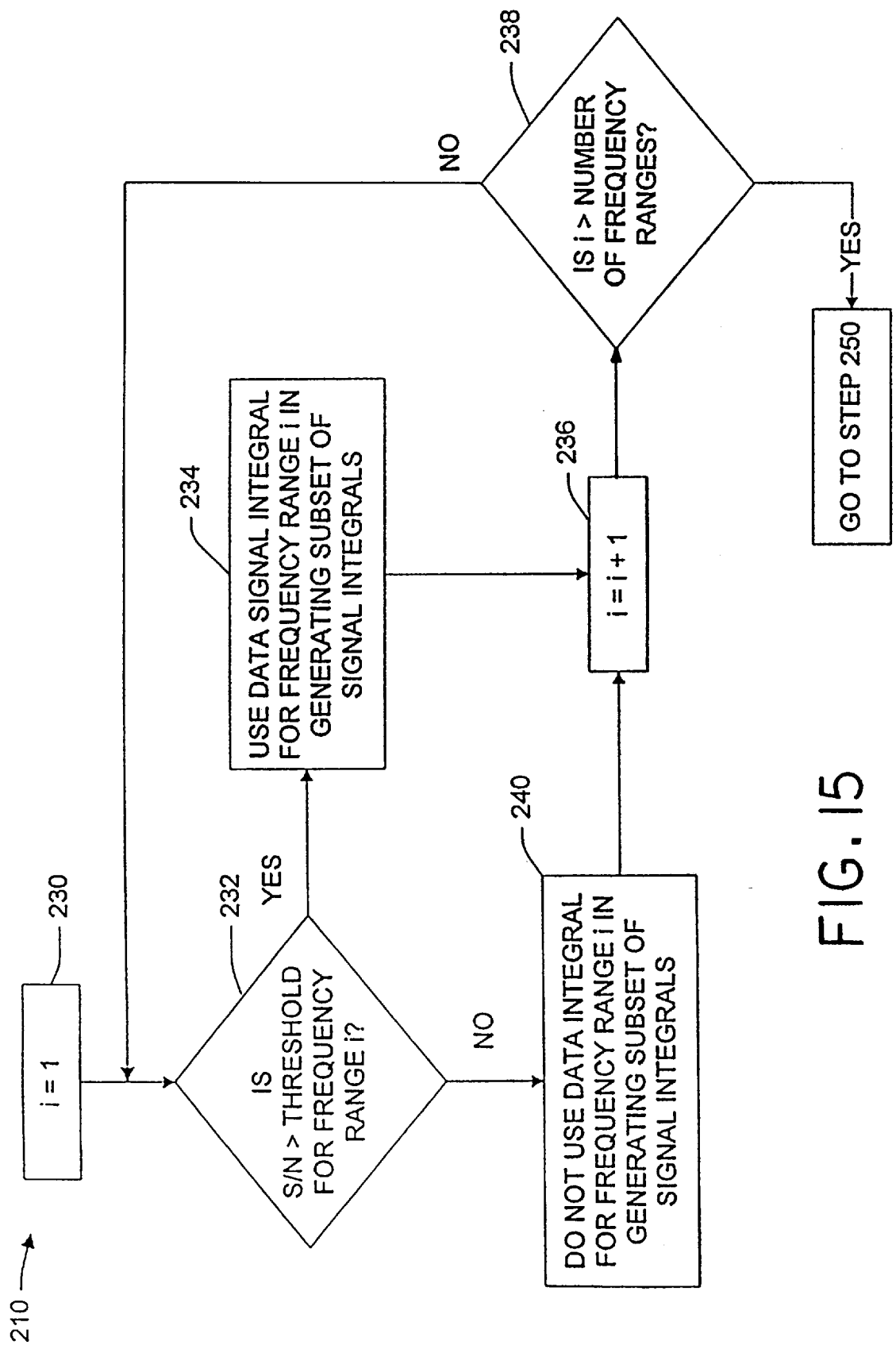
FIG. 15 is a flow chart illustrating a method of selecting a subset of data signal integrals based on signal-to-noise ratios according to the present invention.

The preferred method by which the subset of data signal integrals is selected is illustrated in FIG. 15. A variable "i" is initialized to correspond to the first frequency range in the plurality of frequency ranges at step 230. For the first frequency range (i=1), the signal-to-noise ratio (S/N) is compared to the predetermined threshold at step 232. If the ratio (S/N) exceeds the threshold (YES), the data signal integral for that frequency range is included in a signal integral subset at step 234 and the variable "i" is incremented to correspond to the next frequency range at step 236. The variable "i" is then compared to a number representing the total number of pre-calibrated frequency ranges which are determined empirically at step 238. If the signal-to-noise ratios (S/N) for each of the frequency ranges have not yet been evaluated (NO) at step 238, the signal-to-noise ratio (S/N) for the next frequency range is evaluated at step 232.

Figure 16:
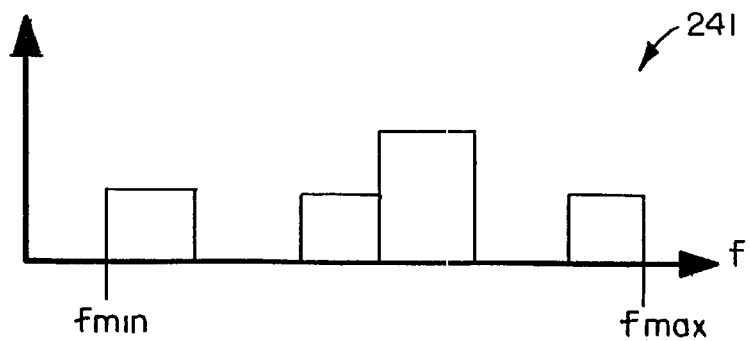
FIG. 16 is a graph illustrating a selected subset of the power spectrum integrals of FIG. 14 based on signal-to-noise ratios according to the present invention.

If at step 232, the signal-to-noise ratio (S/N) of a particular frequency range is not greater than the threshold (NO), the data signal integral corresponding to that particular frequency range is not included in the subset of data signal integrals at step 240. After all the frequency ranges have been analyzed (YES at step 238), a subset of data signal integral 241 having a signal-to-noise ratio (S/N) greater than the predetermined threshold exist, as illustrated in FIG. 16. The number of integrals in the subset are then counted and it is determined whether the subset is large enough to pursue subsequent analysis at step 250 of FIG. 10. For example, if the number of frequency ranges is six (6) and the subset containing high enough signal-to-noise ratios (S/N) is four (4) as illustrated in FIG. 16, then 66% of the data signal integrals 207 are in the subset. This percentage is then compared to a predetermined threshold (preferably 70% which was established experimentally) and if the threshold is not exceeded, then a conclusion is made that not enough data exists to continue the analysis. In this particular example, since 66%<70%, the subset of integrals is not large enough for further analysis and the detection process for that data sample is discontinued.

Returning back to FIG. 10, once the subset of data signal integrals are selected at step 210 (and the number of integrals is sufficient to continue), the subset of integrals 241 is used to detect the presence of a thought at step 250. Once step 250 is complete, a determination is made at step 252 to determine whether a thought has been detected. If the query is answered in the affirmative (YES) (e.g., a sufficient number of data signal integrals exist within the subset) the method 142 moves on to continue the analysis at step 254 where the time window 182 illustrated in FIG. 11 is moved to correspond to a different data segment portion. Preferably the time window 182 (being 16 mSec wide) is shifted 1 mSec to the right and the steps 202–250 of FIG. 10 are repeated again for the new data segment portion. The reason that the process continues at steps 252 and 254 even though a thought has been detected is that the data segment portion that was analyzed in steps 202–250 is only 16 mSec long and more data signal information corresponding to the detected thought may exist in the next neighboring data segment portion (or even in the next 32 mSec data segment). Thus the method 142 continues steps 202–250 until a thought is no longer detected at step 252 (NO) and the next query at step 256 (whether a thought previously was detected is answered in the affirmative (YES)). If a thought had previously been determined at step 252 and is no longer detected, then the method 142 concludes that all the thought data has been detected at step 258 and the method can then proceed to determine the type of thought at step 160 of FIG. 5.

If at step 252 it is determined that a thought has not been detected (NO) and a thought had not been previously detected at step 256, then the method 142 continues its detection process by proceeding to step 254, wherein the time window 182 is preferably shifted to the right with a 1 mSec increment to again begin the process in steps 202–250 of detecting a thought.

Figure 17:
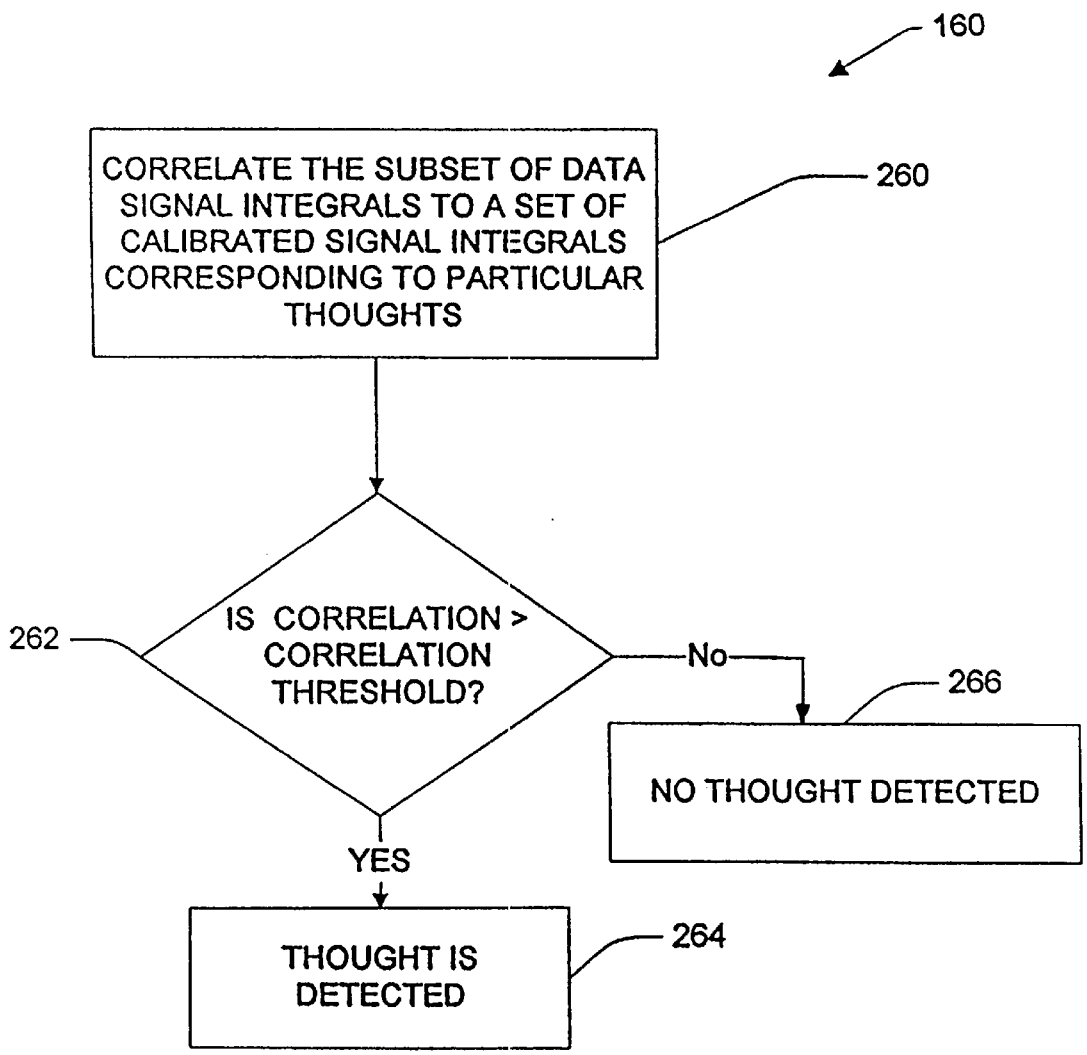
FIG. 17 is a flow chart diagram illustrating a method of using the subset of data signal integrals to detect the presence and type of thought according to the present invention.
Figure 18:
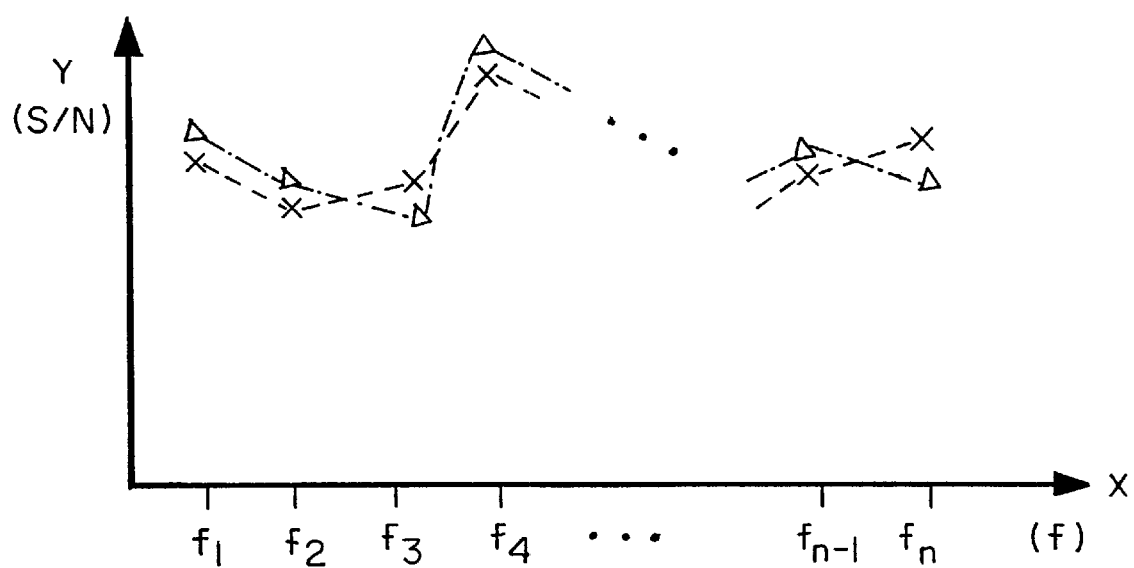
FIG. 18 is a graph illustrating signal-to-noise ratios for a plurality of frequency ranges for two data sets for purposes of correlation of the two data sets.

Once the detection of the thought has been completed at step 258, the type of thought is determined at step 160 of FIG. 5, wherein a preferred method for accomplishing the determination is illustrated in FIGS. 17 and 18. In FIG. 17 the type of thought is determined by correlating the data associated with the subset of data signal integrals corresponding to a detected thought to a set of calibrated data stored in a memory, wherein each of the data sets corresponds to a particular, pre-identified thought at step 260. The correlation is preferably determined as illustrated in FIG. 18, wherein the signal-to-noise ratios (S/N) for each frequency range ($f_1, f_2, \ldots f_n$) is plotted on the Y-axis. In addition, each of the signal-to-noise ratios (S/N) of the data sets are similarly plotted. Thus, as graphically illustrated in FIG. 18, a correlation between the two data sets can be calculated using, for example, the Pearson correlation which is as follows:

$$p(x,y)=\{\Sigma(x-\mathrm{avg}(x))(y-\mathrm{avg}(y))/(\Sigma(x-\mathrm{avg}^2(x))^{1/2})(\Sigma(y-\mathrm{avg}^2(y))^{1/2}),$$

wherein $p(x,y)$ is the correlation coefficient and $\mathrm{avg}(x)$ is $\Sigma x_i$ (for i=1–N and N is the number of frequency ranges). Alternatively, however, other correlation methodologies may also be utilized and each such correlation technique is contemplated as falling within the scope of the present invention.

The correlation coefficient is determined using the detected thought data and each of the stored data sets (which serve as thought signature templates) and compared to a correlation threshold at step 262, which preferably is 50%, although other thresholds may be used. In addition, the threshold may be programmable or user-defined to "tune" the sensitivity of the system. For example, the correlation threshold may be increased if the system is to be tuned for a user-specific application (analogous to speaker dependent voice recognition) while the correlation coefficient may be lowered for use with a plurality of users (analogous to speaker independent voice recognition) as desired. If at step 262 the correlation coefficient for each correlated data set is less than the threshold (NO), then no thought is detected at step 266. If, however, one of the stored data sets does sufficiently correlate with the detected thought at step 262, the type of thought is detected at step 264 and one or more control instructions corresponding to the type of detected thought can then be provided (preferably by retrieving the instructions using a look up table) to effectuate the desired control function.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method of detecting a thought and generating a control instruction corresponding to the thought, comprising the steps of:

detecting the thought by monitoring air pressure near a human ear when the human is thinking the thought; and providing a control instruction corresponding to the detected thought.

2. The method of claim 1, wherein detecting the thought comprises the steps of:

placing a pressure sensor near the ear;

monitoring the air pressure with the pressure sensor;

converting detected air pressure changes to an electrical signal; and processing the electrical signal to detect the thought.

3. The method of claim 2, wherein processing the electrical signal comprises the steps of:

converting the electrical signal to digital signal data;

processing the digital signal data to detect a presence of the thought; and analyzing the processed digital signal data to determine the appropriate control instruction corresponding to the thought.

4. The method of claim 3, wherein processing the digital signal data comprises the steps of:

converting the digital signal data from a time domain to a frequency domain; and processing the frequency domain data to distinguish between noise and the thought.

5. The method of claim 3, wherein processing the digital signal data comprises the steps of:

(a) separating the data into a plurality of data segments;

(b) analyzing a first data segment for the detection of a thought;

(c) analyzing a next data segment for the detection of a thought;

(d) analyzing all the analyzed data segments together for the detection of a thought; and (e) repeating steps (c) and (d) until all the data segments are analyzed.

6. The method of claim 3, wherein processing the digital signal data comprises the steps of:

(a) selecting a segment of the digital signal data corresponding to a time window;

(b) converting a portion of the data segment from a time domain to a frequency domain;

(c) calculating a power spectrum for the converted data portion;

(d) calculating integrals of the power spectrum of the converted data portion for a plurality of frequency ranges;

(e) calculating a plurality of signal-to-noise ratios using the converted data portion integrals and integrals for a power spectrum of a noise signal for the plurality of frequency ranges;

(f) selecting a subset of the converted data portion integrals based on the signal-to-noise ratios; and (g) evaluating the subset of converted data portion integrals to detect a presence of the thought.

7. The method of claim 6, further comprising the steps of:

selecting another segment of the digital signal data corresponding to another time window, wherein the time windows partially overlap; and repeating the steps of (b)–(g) until a thought is detected or all the digital signal data has been evaluated.

8. The method of claim 6, wherein selecting a subset of the converted data portion integrals comprises the steps of:

comparing the signal-to-noise ratios for each of the frequency ranges to a predetermined threshold value;

selecting the converted data portion integrals corresponding to the frequency ranges if the signal-to-noise ratios are greater than the predetermined threshold value; and using the selected subset of converted data portion integrals for subsequent analysis.

9. The method of claim 8, further comprising the steps of:

comparing a number of the converted data portion integrals in the selected subset to a threshold value; and disregarding the portion of data if the number falls below a threshold value.

10. The method of claim 6, wherein evaluating the subset of integrals comprises the steps of:

correlating the subset of integrals with a plurality of integral sets corresponding to a plurality of thoughts; and selecting one of the plurality of thoughts as the detected thought if the correlation between the subset of integrals and the integral set corresponding the one of the plurality of thoughts is greater than a predetermined threshold.

11. The method of claim 10, wherein the integral sets corresponding to the plurality of thoughts are generated by a user via a thought calibration process.

12. The method of claim 11, wherein the thought calibration process comprises the steps of:

(a) placing the air pressure sensor near the ear of a human;

(b) having the human think a particular thought at least one time;

(c) recording the air pressure during the thinking process; and (d) generating a set of integrals corresponding to the particular thought for subsequent correlation.

13. The method of claim 12, comprising repeating steps (a)–(d) for a plurality of thoughts, thereby generating a set of integrals for a plurality of thoughts.

14. The method of claim 1, wherein monitoring the air pressure comprises the steps of:

placing a microphone near the ear; and converting a change in air pressure to an analog electrical signal using the microphone.

15. A system for detecting a thought and generating a control instruction corresponding to the thought, comprising:

a pressure sensor for sensing a pressure near a human ear when the human is thinking the thought, wherein the sensor produces an electrical signal corresponding to the pressure;

a processor for processing the electrical signal to detect the thought and generating the control instruction in response to the detection; and an output peripheral for receiving the control instruction from the processor and providing an output corresponding to the control instruction.

16. The system of claim 15, further comprising an analog to digital converter for converting an analog signal from the pressure sensor into a digital signal for subsequent processing by the processor.

17. The system of claim 15, wherein the pressure sensor comprises a microphone.

18. The system of claim 17, wherein the microphone is affixed near the human ear with an attachment means and substantially isolated from external pressure noise.

19. The system of claim 15, wherein the output peripheral is at least one of a display, a robot, a mechanical apparatus, a medical device and a game.

20. A method of detecting a thought, comprising detecting the thought by monitoring air pressure near a human ear.

* * * * *